US006607799B1

(12) United States Patent
Heinecke et al.

(10) Patent No.: US 6,607,799 B1
(45) Date of Patent: Aug. 19, 2003

(54) SURGICAL DRESSING WITH DELIVERY SYSTEM AND METHOD OF MANUFACTURE

(75) Inventors: Steven B. Heinecke, New Richmond, WI (US); Donald G. Peterson, Shoreview, MN (US); Karen M. Bisbee, Maplewood, MN (US); Richard L. Jacobson, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/172,815

(22) Filed: Oct. 15, 1998

(51) Int. Cl.[7] .............................. A61L 15/16; C09J 7/04

(52) U.S. Cl. .................... 428/40.1; 428/41.7; 428/41.8; 428/42.2; 428/42.3; 428/43; 602/52; 602/54; 602/55; 602/57; 602/58; 602/59

(58) Field of Search .............................. 428/40.1, 41.7, 428/41.8, 42.2, 42.3, 43; 602/52, 54, 55, 57, 58, 59

(56) References Cited

U.S. PATENT DOCUMENTS

| | | | | |
|---|---|---|---|---|
| 2,532,011 A | | 11/1950 | Dahlquist et al. | 154/53.5 |
| RE24,906 E | | 12/1960 | Ulrich | 206/59 |
| 3,389,827 A | | 6/1968 | Abere et al. | 220/53 |
| 3,645,835 A | | 2/1972 | Hodgson | 161/146 |
| 4,112,213 A | | 9/1978 | Waldman | 526/279 |
| 4,310,509 A | | 1/1982 | Berglund et al. | 424/28 |
| 4,323,557 A | | 4/1982 | Rosso et al. | 424/28 |
| 4,472,480 A | | 9/1984 | Olson | 428/332 |
| 4,513,739 A | | 4/1985 | Johns | 128/156 |
| 4,545,371 A | | 10/1985 | Grossmann et al. | 128/132 D |
| 4,595,001 A | | 6/1986 | Potter et al. | 128/156 |
| 4,598,004 A | | 7/1986 | Heinecke | 428/40 |
| 4,726,972 A | * | 2/1988 | Instance | 428/40 |
| 4,737,410 A | | 4/1988 | Kantner | 428/343 |
| 4,753,232 A | | 6/1988 | Ward | 128/156 |
| 4,832,008 A | | 5/1989 | Gilman | 128/155 |
| 4,884,563 A | | 12/1989 | Sessions | 128/155 |
| 4,926,850 A | | 5/1990 | Lott et al. | 128/155 |
| 4,941,882 A | | 7/1990 | Ward et al. | 604/180 |
| RE33,353 E | | 9/1990 | Heinecke | 428/40 |
| 5,088,483 A | | 2/1992 | Heinecke | 602/46 |
| 5,153,040 A | | 10/1992 | Faasse, Jr. | 428/40 |
| 5,160,315 A | | 11/1992 | Heinecke et al. | 602/57 |
| 5,266,371 A | | 11/1993 | Sugii et al. | 428/40 |

(List continued on next page.)

FOREIGN PATENT DOCUMENTS

| | | |
|---|---|---|
| EP | 0 035 399 | 9/1981 |
| EP | 0 035 399 A2 | 9/1981 |
| EP | 0 051 935 | 5/1982 |
| EP | 0 051 935 A2 | 5/1982 |
| EP | 0 437 944 | 7/1991 |
| EP | 0 437 944 A1 | 7/1991 |
| GB | 1280631 | 7/1972 |
| WO | WO 98/29516 | 7/1998 |

*Primary Examiner*—Sandra M. Nolan
(74) *Attorney, Agent, or Firm*—Nancy M. Lambert

(57) ABSTRACT

Adhesive composite dressings with simple and inexpensive delivery systems and methods of manufacturing the dressings are disclosed. The dressings include liners having a release surface and a retention surface. The bond strength between the liner and the pressure sensitive adhesive in the area of the retention surface is greater than the bond strength between the liner and the pressure sensitive adhesive in release surface. The increased bond strength in the area of the retention surface allows the backing to be held taut during delivery to assist in smooth aseptic delivery of the dressing. The retention surfaces can be provided by abrasion, embossing, perforating the liner, or combinations thereof. In addition, the methods of manufacturing the dressings can be practiced in-line with other converting operations using standard release liners.

26 Claims, 6 Drawing Sheets

U.S. PATENT DOCUMENTS

| | | | | | |
|---|---|---|---|---|---|
| 5,411,295 | A | | 5/1995 | Bates et al. | 283/81 |
| 5,520,629 | A | | 5/1996 | Heinecke et al. | 602/57 |
| 5,531,855 | A | | 7/1996 | Heinecke et al. | 156/252 |
| 5,722,943 | A | | 3/1998 | Sessions | 602/57 |
| 5,733,251 | A | | 3/1998 | Johns | 602/57 |
| 5,738,642 | A | | 4/1998 | Heinecke et al. | 602/58 |
| 5,849,325 | A | | 12/1998 | Heinecke et al. | 424/443 |
| 5,951,505 | A | * | 9/1999 | Gilman et al. | 602/41 |
| 5,968,000 | A | | 10/1999 | Harrison et al. | 602/41 |
| 6,197,397 | B1 | * | 3/2001 | Sher et al. | 428/42.3 |

* cited by examiner

SURGICAL DRESSING WITH DELIVERY SYSTEM AND METHOD OF MANUFACTURE

FIELD OF THE INVENTION

The present invention relates to pressure-sensitive adhesive composites having a delivery system and methods of using the composites as well as methods of manufacturing the composites. In particular, the present invention is useful in connection with very thin high moisture vapor permeable film wound dressings.

BACKGROUND OF THE INVENTION

The use of transparent film dressing continues to grow at an accelerated rate. In addition to their use as protective layers over wounds, where they facilitate healing in a moist environment while acting as a barrier to contaminating liquids and bacteria, the films are also used over catheters to prevent contamination of the catheter insertion site by contaminating liquids and bacteria. The films may also be used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), OP-SITE™ (T.J. Smith & Nephew, Hull, England), and UNIFLEX™ (How Medica, Largo, Fla.).

The polymeric films used in those dressings and drapes, referred to as dressings below, are typically conformable. In other words, the films are extremely flimsy, flexible, and supple. They are typically supplied with a releasable protective liner covering the adhesive coated surface of the film. When the liner is removed, the adhesive coated film tends to wrinkle and adhere to itself, interfering with the smooth aseptic application of the dressing to a patient's skin. Various delivery systems have been proposed to address this problem.

U.S. Pat. No. 5,153,040 (Faase, Jr.) discloses dressing delivery systems in which a two-part liner is provided to protect the pressure sensitive adhesive on the bottom face of the film. Each liner includes an adhesion enhancement strip which is preferably permanently affixed to the pressure sensitive adhesive and film backing. During delivery, the adhesion enhancement strips are separated from the remainder of the film along perforation lines on opposite ends of the dressing. One disadvantage with this process is that it requires additional components, i.e., the adhesion enhancement strips located between the liner and the film, to accomplish the delivery system. Those additional components add to the cost and complexity of manufacturing the dressings.

U.S. Pat. No. 4,513,739 (Johns) discloses dressing delivery systems which also include a two-part liner and means for retarding weakness of the release liner from the adhesive on the film at opposite ends of the dressing. Like the delivery system described above, however, this system also requires the addition of components to the dressing to provide the differential release characteristics at the ends of the dressing. Among the additional components are different adhesives, backings with varying layer thicknesses, additional layers secured to the backing, folds in the liner such that the liner is directly connected to the backing over the ends of the dressing (see FIG. 5), and additional components added to the ends of the dressing that attach the liner to the backing (see FIG. 6). As above, the additional components add to the cost and complexity of manufacturing the dressings.

U.S. Pat. No. Re. 33,353 (Heinecke) discloses a dressing delivery system in which the liners are strip-coated with a release agent such that the ends of the liners are free of release coatings, which increases their adhesion to the pressure-sensitive adhesive on the bottom face of the backing. As a result, the backing can be suspended between two liners during delivery. After delivery, the end portions of the backing are preferably removed along with the attached liner. One disadvantage with this approach is that the strip-coated liner material must be stocked separately from liners in which the entire surface includes a release coating, thereby adding to the cost of manufacturing the dressings.

SUMMARY OF THE INVENTION

The present invention provides adhesive composite dressings with simple and inexpensive delivery systems. The dressings include liners having a release surface and a retention surface. The bond strength between the liner and the pressure sensitive adhesive in the area of the retention surface is greater than the bond strength between the liner and the pressure sensitive adhesive in release surface. The increased bond strength in the area of the retention surface allows the backing to be held taut during delivery to assist in smooth aseptic delivery of the dressing. The retention surfaces can be provided by abrasion, embossing, perforating the liner, or combinations thereof.

Advantages of the delivery systems provided by the present invention include the simplicity and ease with which the dressings can be manufactured. For example, a standard liner with a fully coated release surface can be used with the retention surfaces being formed in-line during the converting process. As a result, no special liners are needed in inventory.

A further advantage of the notched dressings of the present invention is that the notched portions of the dressing are maintained in tension, thereby assisting in delivery of the notched dressings over catheter insertion sites.

In one aspect, the present invention provides an adhesive composite dressing including a backing having top and bottom faces and opposing first and second edges; a pressure sensitive adhesive located on the bottom face of the backing; a liner comprising a release surface and an abraded surface, wherein the abraded surface is attached to the pressure sensitive adhesive along the first edge of the backing; and a handle attached to the backing along the second edge of the backing.

In another aspect, the present invention provides an adhesive composite dressing including a backing having top and bottom faces and opposing first and second edges; a pressure sensitive adhesive located on the bottom face of the backing; a first liner sheet including a first release surface attached to a portion of the pressure sensitive adhesive and a first abraded surface attached to the pressure sensitive adhesive along the first edge of the backing, wherein the strength of the bond between the first abraded surface and the pressure sensitive adhesive is greater than the strength of the bond between the first release surface and the pressure sensitive adhesive; and a second liner sheet including a second release surface attached to a portion of the pressure sensitive adhesive and a second abraded surface attached to the pressure sensitive adhesive along the second edge of the backing, wherein the strength of the bond between the second retainer and the pressure sensitive adhesive is greater than the strength of the bond between the second release surface and the pressure sensitive adhesive.

In another aspect, the present invention provides an adhesive composite dressing including a backing having top and bottom faces and opposing first and second edges; a pressure sensitive adhesive located on the bottom face of the backing; a liner comprising a release surface and a retention surface, the retention surface including a discontinuous release coating, wherein the retention surface is attached to the pressure sensitive adhesive along the first edge of the backing; and a handle attached to the backing along the second edge of the backing.

In another aspect, the present invention provides an adhesive composite dressing including a backing having top and bottom faces and opposing first and second edges; a pressure sensitive adhesive located on the bottom face of the backing; a first liner sheet including a first release surface attached to a portion of the pressure sensitive adhesive and a first retention surface including a discontinuous release coating, the first retention surface being attached to the pressure sensitive adhesive along the first edge of the backing, wherein the strength of the bond between the first retention surface and the pressure sensitive adhesive is greater than the strength of the bond between the first release surface and the pressure sensitive adhesive; and a second liner sheet including a second release surface attached to a portion of the pressure sensitive adhesive and a second retention surface including a discontinuous release coating, the second retention surface being attached to the pressure sensitive adhesive along the second edge of the backing, wherein the strength of the bond between the second retention surface and the pressure sensitive adhesive is greater than the strength of the bond between the second release surface and the pressure sensitive adhesive.

In another aspect, the present invention provides an adhesive composite dressing including a backing having top and bottom faces and opposing first and second edges; a pressure sensitive adhesive located on the bottom face of the backing; and a liner including a release surface attached to the pressure sensitive adhesive and a void formed through the liner, the void exposing a portion of the pressure sensitive adhesive, wherein the bond strength between the liner and the pressure sensitive adhesive is increased proximate the void.

In another aspect, the present invention provides an adhesive composite dressing including a backing having top and bottom faces and opposing first and second edges; a pressure sensitive adhesive located on the bottom face of the backing; a first liner sheet including a first release surface attached to a portion of the pressure sensitive adhesive and a first void exposing a first portion of the pressure sensitive adhesive; and a second liner sheet including a second release surface attached to a portion of the pressure sensitive adhesive and a second void exposing a portion of the pressure sensitive adhesive.

In another aspect, the present invention provides an adhesive composite dressing including a backing having top and bottom faces, opposing first and second edges; a pressure sensitive adhesive located on the bottom face of the backing; a liner attached to the pressure sensitive adhesive; means for increasing the bond strength between the liner and the pressure sensitive adhesive proximate the first edge of the backing; and a notch formed in the backing, pressure sensitive adhesive, and the liner, wherein the notch opens along the first edge of the backing and extends towards the second edge of the backing.

In another aspect, the present invention provides a method of manufacturing an adhesive composite dressing by providing a backing having top and bottom faces; providing pressure sensitive adhesive on the bottom face of the backing; providing a liner having a release surface and at least one retention surface; and attaching the release surface and the retention surface of the liner to the pressure sensitive adhesive on the backing.

These and other features and advantages of the articles and methods of the present invention are discussed below.

DETAILED DESCRIPTION OF ILLUSTRATIVE EMBODIMENTS OF THE INVENTION

Figure 1:
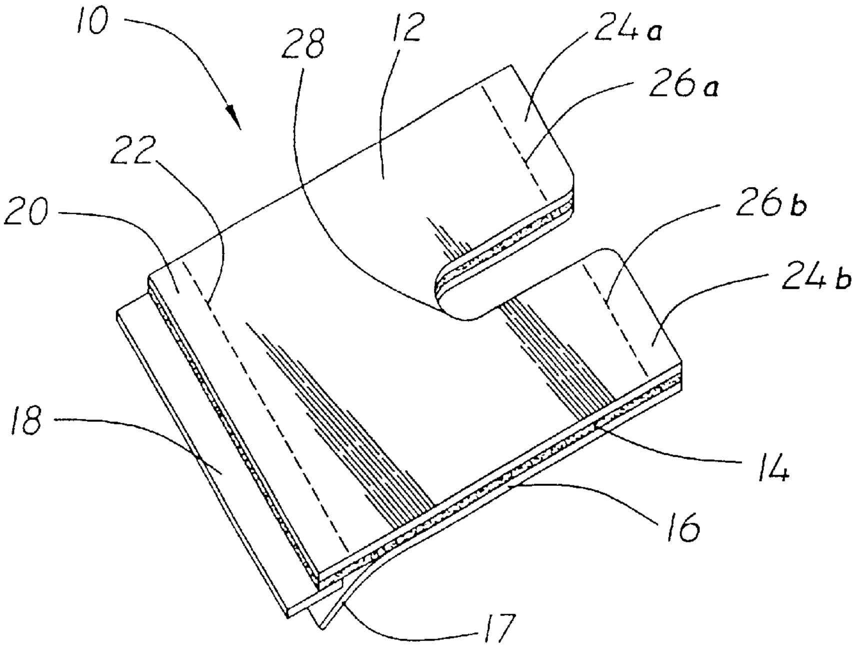
FIG. 1 is a perspective view of one adhesive composite dressing according to the present invention.

The present invention is particularly useful in the field of pressure sensitive adhesive dressings having high moisture vapor permeable film backings. Issued U.S. Pat. Nos. 3,645,835 and 4,595,001 and European Patent Application Publication No. 0 437 944 describe methods of making such films and methods for testing their permeability. Preferably, the film/adhesive composite dressings should transmit moisture vapor at a rate equal to or greater than human skin. In one aspect, the adhesive coated film may advantageously transmit moisture vapor at a rate of at least 300 $g/m^2/24$ hrs/37° C./100–10% RH, more preferably at least 700 $g/m^2/24$ hrs/37° C./100–10% RH, and most preferably at least 2000 $g/m^2/24$ hrs/37° C./100–10% RH using the inverted cup method as described in U.S. Pat. No. 4,595,001.

The backing film is also preferably conformable to anatomical surfaces. As such, when the backing is applied to an anatomical surface, it conforms to the surface even when the surface is moved. The preferred backing is also conformable to anatomical joints. When the joint is flexed and then returned to its unflexed position, the backing stretches to accommodate the flexion of the joint, but is resilient enough to continue to conform to the joint when the joint is returned to its unflexed condition. A description of this characteristic of backings preferred for use with the present invention can be found in issued U.S. Pat. Nos. 5,088,483 and 5,160,315.

A description of some backings that may be preferred for use in the adhesive composite security articles of the present invention can be found in issued U.S. Pat. Nos. 5,088,483 and 5,160,315, as well as European Patent Application Publication No. 0 437 944.

Particularly preferred film backings may be selected from the group of elastomeric polyurethane, polyester, or polyether block amide films, or combinations thereof. These films combine the desirable properties of resiliency, high moisture vapor permeability, and transparency that may be preferred in the backings. Also, although the backings are depicted below as monolayer articles, it will be understood that they could include multiple layers as described in, e.g., European Patent Application Publication No. 0 437 944.

The preferred pressure sensitive adhesives which can be used in the adhesive composites of the present invention are the normal adhesives which are applied to the skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl acrylate: ethyleneoxide acrylate:acrylic acid terpolymer, as described in U.S. Pat. No. 4,737,410 (see Example 31). Other useful adhesives are described in U.S. Pat. Nos. 3,389,827; 4,112,213; 4,310,509; and 4,323,557; as well as UK Patent No. 1280631 (see, e.g., polyvinyl ether adhesives) and European Patent Nos. 35399 and 51935. Inclusion of medicaments or antimicrobial agents in the adhesive is also contemplated, as described in U.S. Pat. Nos. 4,310,509 and 4,323,557.

The preferred pressure sensitive adhesives described above preferably transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001.

In the preferred embodiments according to the present invention, the choice of adhesives is limited to those that are safe to use on human or animal skin, and preferably to those that are of the class known as "hypoallergenic" adhesives. The preferred acrylate copolymers are adhesives of this class.

In addition to moisture vapor permeability and hypoallergenicity, it may also be preferred that the adhesives used in connection with the adhesive composite security articles of the present invention exhibit high initial tack upon application to the skin or the surface of a nail. One such adhesive is described in commonly-assigned, co-pending U.S. Pat. No. 5,849,325, titled "Moisture-Regulated Adhesive Dressing" and other useful adhesives may include polyvinyl ether adhesives as discussed in, e.g., UK Patent No. 1280631. One advantage of an adhesive exhibiting high initial tack is additional securing of, e.g., a catheter by the dressing may be ore quickly enhanced as opposed to adhesives that have a lower initial tack.

Liners are available from a variety of manufacturers in a wide variety of proprietary formulations. Those skilled in the art will normally test those liners in simulated use conditions against an adhesive of choice to arrive at a product with the desired release characteristics. The materials used to supply the handles and liners for dressings manufactured according to the present invention is preferably substantially more rigid than the backing.

The adhesive composite dressings of the present invention may also include a low adhesion coating on a top face of the backing, which is preferably coated as a solution of polyvinyl N-octadecyl carbamate and a blend of silicone resins, as described in U.S. Pat. No. 5,531,855. While it is preferred that the top face of the adhesive composites of the present invention include a low adhesion coating, adhesive composites without such a coating are also considered to be within the scope of the present invention.

FIG. 1 is a perspective view of one embodiment of an adhesive composite dressing according to the present invention. The dressing 10 includes a backing 12 having a top and bottom face, with a pressure sensitive adhesive 14 located on the bottom face. A liner 16 is located over the adhesive 14 to protect it until delivery to a patient. The liner 16 preferably includes a liner tab 17 whose purpose will be described more completely below.

Also attached to the pressure sensitive adhesive 14 is a handle 18 useful in delivery of the dressing 10 to a patient. The handle 18 and the liner tab 17 preferably overlap each other such that they provide a convenient location to separate the liner 16 from the pressure-sensitive adhesive 14 to deliver the dressing 10 to a patient.

The backing 12 also preferably includes a first line of weakness 22 located along a first edge of the backing 12. The line of weakness 22 is preferably provided as a line of perforations, although other lines of weakness are contemplated. The line of weakness 22 defines a portion of the backing 12 which will be referred to below as the delivery strip 20. The handle 18 is preferably connected to the delivery strip 20 of the backing 12 such that it does not overlap the backing 12 past the location of the first line of weakness 22.

At the opposing second edge of the backing 12, a pair of delivery strips **24*a* and 24*b* (referred to collectively as delivery strip 24) are defined by lines of weakness 26*a* and 26*b* located on each side of the notch 28 formed in the dressing 10. The lines of weakness 26*a* and 26*b* will be collectively referred to as the second line of weakness 26** below.

In the illustrated embodiment of the dressing 10, notch 28 is provided through the backing 12, pressure-sensitive adhesive 14, and liner 16. The notch 28 include an opening in the second edge of the dressing 10 and extend generally towards the first edge of the dressing 10. The notch 28 is useful in connection with ported catheters, as will be described more completely below.

Figure 2:
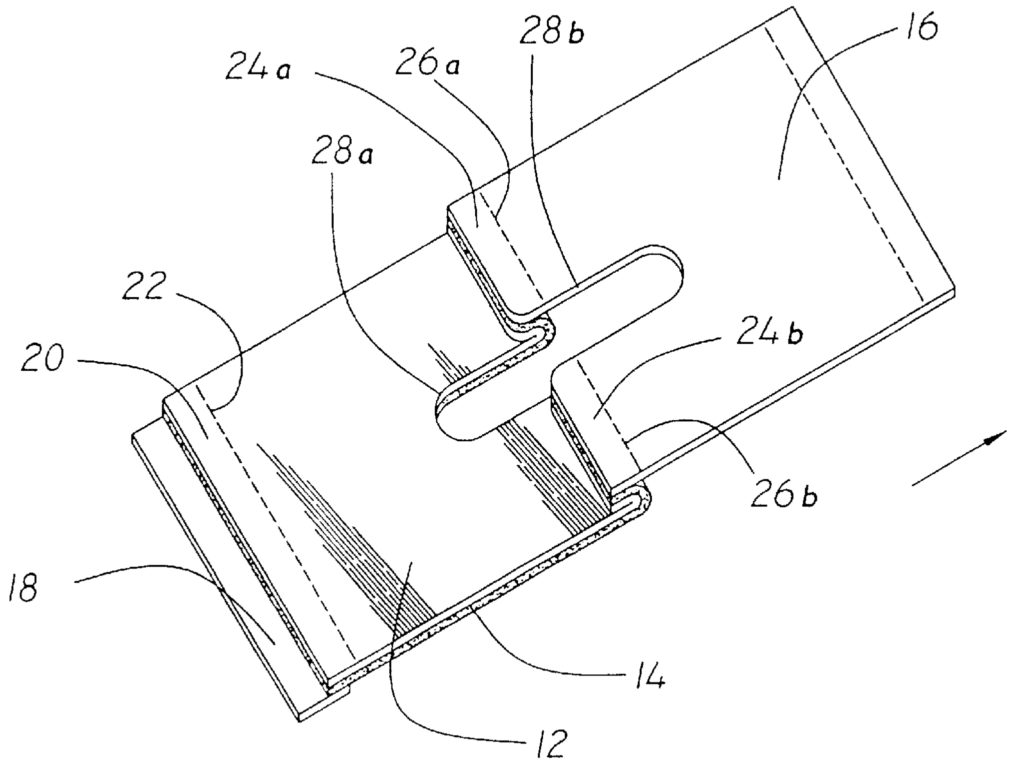
FIG. 2 is a perspective view of the dressing of FIG. 1 with the liner partially removed from the pressure-sensitive adhesive on the bottom of the backing such that the dressing is ready for placement on a patient.

FIG. 2 illustrates the delivery process in which the liner 16 has been substantially removed from contact with the pressure-sensitive adhesive 14 on the backing 12. Although not shown, the user preferably holds the handle 18 and tab 17 of the liner 16 and separates them to suspend the backing 12 between the handle 18 and liner 16.

Because the backing is preferably held taut between the handle 18 and liner 16 to prevent the backing 12 from folding or wrinkling after removal of the liner 16, the bond strength between the liner 16 and the pressure-sensitive adhesive 14 in the area of the delivery strips 20 and 24 is preferably greater than the bond strength between the liner 16 and the remainder of the pressure-sensitive adhesive 14 located between the delivery strips 20 and 24. As a result, as the user separates the liner 16 from the pressure-sensitive adhesive 14, tension can be applied to the backing 12 as the release line between the liner 16 and pressure sensitive adhesive 14 reaches the delivery strip 24 along the second edge of the backing 12. The result is that during delivery a user may grasp the liner 16 and the handle 18 and remove the liner 16 from a substantial portion of the backing 12 to place it in tension, thereby reducing the likelihood that the backing will fold or wrinkle during delivery.

Figure 1A:
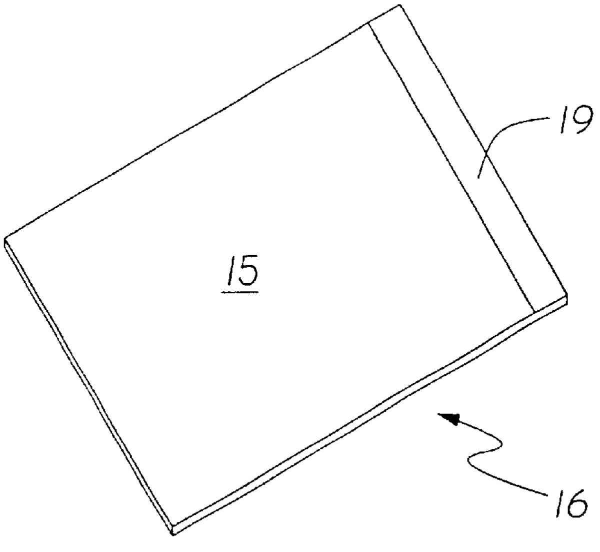
FIG. 1A is a perspective view of a liner.

The top face of one liner 16 is illustrated in FIG. 1A and includes a release coating located on a release surface 15 and a retention surface 19 located along an edge of the liner 16. It is preferred that the retention surface 19 be located along an edge of the backing 12 and, more preferably, that the retention surface correspond roughly to the delivery strip 24 of the backing 12 in size and location. To place the backing 12 in tension as described above, the bond strength between the release surface 15 and the pressure sensitive adhesive 14 is lower than the bond strength between the retention surface 19 and the pressure sensitive adhesive 14. Similarly, the bond strength between the handle 18 and the backing 12/pressure sensitive adhesive 14 composite is preferably greater than the bond strength between the release surface 15 and the pressure sensitive adhesive 14.

The increased bond strength between the liner 16 and the pressure sensitive adhesive 14 in the area of the retention surface 19 can be provided through a number of techniques for disrupting the continuity of a release coating on the liner 16. By disrupting the continuity of the release coating, the pressure sensitive adhesive 14 may be able to bond with the underlying liner 16 directly which typically results in a stranger bond as compared to the bond strength of the pressure sensitive adhesive 14 and the release coating.

In one embodiment, the increased bond between the pressure sensitive adhesive 14 and the retention surface 19 can be provided by abrading a release coating from the liner 16 to form an abraded surface in which at least a portion of the release coating, or potentially all of the release coating, is removed from the liner 16 in the area of the retention surface 19. The amount of release coating removed by abrasion in the retention surface 19 can be varied to control the strength of the bond between the retention surface 19 and the pressure sensitive adhesive 14.

Where smaller portions of the release coating are removed by abrasion, the bond strength may be only slightly increased, allowing the retention surface 19 to separate or release from the pressure sensitive adhesive 14/backing 12 composite. In those embodiments, the lines of weakness 26 illustrated in connection with the dressing 10 may not be required. One advantage to such embodiments is that all of the backing 12 is delivered to the patient, with none of the backing 12 being discarded with the liner 16 after delivery.

Where larger amounts of the release coating, such as all or substantially all of the release coating, are removed from the liner 16 in the area of the retention surface 19, the bond strength between the retention surface 19 and the pressure sensitive adhesive 14 may be too great to allow removal of the retention surface 19 from the pressure sensitive adhesive 14 without undesirable stretching of the backing 12. In those situations, it may be preferred that a line of weakness 26 be provided in the backing 12 as illustrated to allow separation of the backing 12 before the bond between the pressure sensitive adhesive 14 and a patient's skin is compromised by stretching of the backing 12 during removal of the liner 16.

Where a line of weakness 26 is provided in the backing 12, the bond strength between the retention surface 19 of the liner 16 and the pressure sensitive adhesive 14 in the area of the delivery strip 24 is preferably greater than the tensile strength of the backing 12 across the line of weakness 26. As a result, after proper location of the dressing 10 on a patient's skin such that the exposed pressure-sensitive adhesive 14 is adhered to the skin, the backing 12 can be smoothed down and increased tension is applied to the backing 12 by pulling the liner 16 away from the backing 12. The increased tension preferably causes the film backing 12 to separate along line of weakness 26. After separation, the delivery strip 24 is removed from the backing 12 along with liner 16, without separation of the retention surface 19 of the liner 16 from the delivery strip 24.

In those dressings in which it is desired that the handle 18 be separable from the remainder of the dressing 10 after delivery and in which the handle 18 is attached to the pressure sensitive adhesive 14 on the backing 12, the bond strength between the handle 18 and the pressure-sensitive adhesive 14 may also be controlled through abrasion of a release coating on the handle as described with respect to the liner 16 above. In other words, the bond between the handle 18 and the pressure sensitive adhesive 14 can be controlled to allow removal of the handle 18 from the pressure sensitive adhesive 14 without significantly stretching the backing 12 to the point at which the bond between the pressure sensitive adhesive and the patient's skin is unacceptably compromised. In such embodiments where the bond between the handle 18 and the pressure sensitive adhesive 14 is releasable, no line of weakness is required and none of the backing 12 is removed with the handle 18.

In other embodiments such as the one depicted in FIGS. 1 and 2, the handle 18 is not releasably attached to the pressure sensitive adhesive 14 and a line of weakness 22 is provided. In such an embodiment, the handle 18 may include an abraded surface from which substantially all of a release coating has been removed from the handle 18. The backing 12 preferably separates preferably separates along the line of weakness 22 during removal of the handle 18 because the strength of the bond between the handle 18 and the pressure sensitive adhesive 14 is greater than the tensile strength of the backing 12 across the line of weakness 22. As a result, removal of the handle 18 also removes the delivery strip 20 portion of the backing 12 along the line of weakness 22.

The lines of weakness 22 and 26 in the illustrated embodiment of dressing 10 may be provided in the form of perforations. The dimensions of the perforations vary based on the backing 12 and other factors, although too few perforations or perforations that are too small can result in stretching, deformation and uneven weakness of the backing 12. At the other end of the spectrum, too many perforations or perforations that are too large can result in backings 12 that separate too easily, thereby inhibiting the tension that can be applied to the backing 12 between the handle 18 and liner 16. The result is that smooth delivery of the backing 12 can be inhibited.

Although the liner 16 and handle 18 have been described as including abraded surfaces from which a portion or all of a release coating has been removed, the dressings according to the present invention may alternatively be manufactured with embossed liners 16 and handles 18 to increase the strength of the bond between the pressure sensitive adhesive 14 and the liner 16 and/or handle 18.

Embossing a release coated surface can increase the bond strength between that surface and a pressure sensitive adhesive by disrupting the continuity of the release coating in the embossed areas. That discontinuous release coating increases bond strength by allowing tie pressure sensitive adhesive 14 access the materials underneath the release coating. For example, a liner 16 could include a retention surface 19 that is embossed instead of, or in addition to, abrading as discussed above. The exact nature of the embossing used in the retention surface 19 can vary based on, e.g., the pressure sensitive adhesive 14, the release coating, the liner material, whether the dressing is gamma sterilized (which can increase the bond strengths), etc.

The embossed retention surface 19 could be releasably attached to the pressure sensitive adhesive 14 in which case no line of weakness 26 is required to allow removal of the liner 16 from the dressing 10. Alternatively, the embossing could cause enough disruption in the release coating such that a line of weakness 26 would be desirable to prevent excessive stretching of the backing 12 when removing the liner 16.

The handle 18 could include an embossed surface similar to that used in connection with the liner 16 to achieve either a desired releasable handle 18 or a handle 18 that is more securely attached to the backing 12, thereby requiring a line weakness 22 along which the backing 12 separates during removal of the handle 18.

Figure 3:
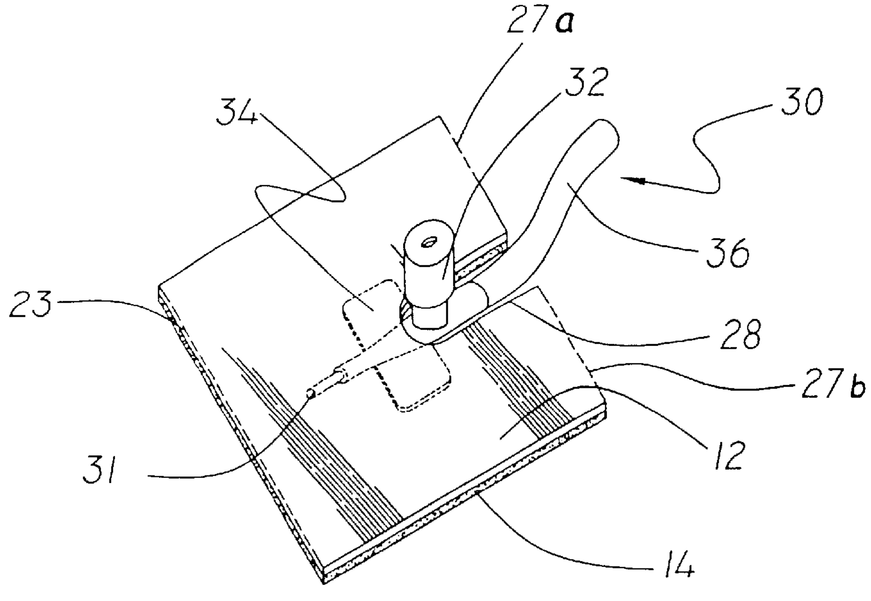
FIG. 3 is a perspective view of a dressing according to the present invention located over a catheter on a patient.

FIG. 3 illustrates the backing 12 of FIGS. 1 and 2 in place over a catheter 30 after the release liner 16 and the handle 18 have been removed. The edges 23, 27*a,* and 27*b* of the backing 12 are formed along the lines of weakness 22 and 26, as described above. The backing 12 is preferably sized to assure that the insertion site 31 of the catheter 30 is covered by the backing 12 and pressure-sensitive adhesive 14. It is further preferred that the backing 12 and pressure-sensitive adhesive 14 offer adequate support to the wings 34 of the catheter 30. The notch 28, formed in the second edge of the backing 12, is positioned over the catheter hub 32 and allows connection of the extension tubing set 36 to the catheter 30 as desired.

Returning to FIG. 2, the notch 28 formed through the backing 12, pressure-sensitive adhesive 14, and liner 16 preferably opens into a void defined by a backing notch 28*a* and a liner notch 28*b*. It is preferred that the larger opening formed during delivery of the dressing 10 assists in its placement over a catheter 30, as depicted in FIG. 3. Furthermore, it is advantageous that the backing 12 is supported on both sides of the notch 28*a* by the unitary liner 16 to reduce the likelihood of wrinkling or folding of the backing 12 in the area around the notch 28*a*. It will be understood that although the notch 28 formed in the dressing 10 includes a liner notch 28*b,* it may be possible in some instances to remove only the backing and pressure-sensitive adhesive in the area of the notch 28 while leaving substantially all of the liner 16 in place.

Figure 4:
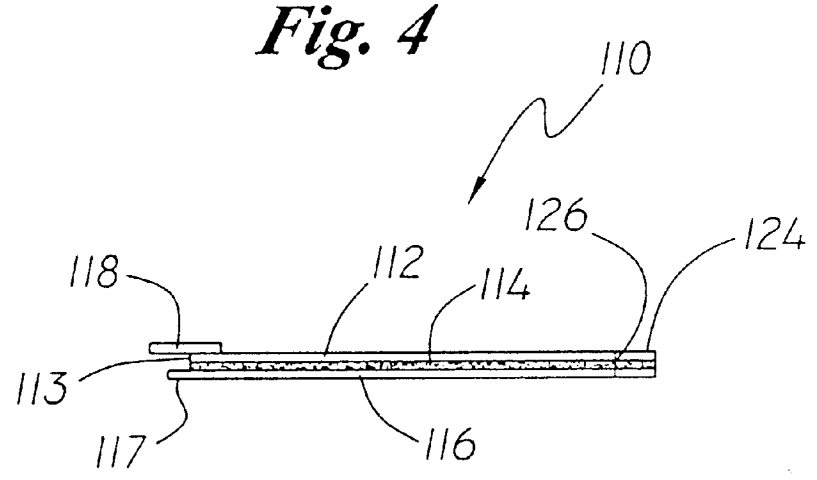
FIG. 4 is a side view of the dressings of FIGS. 1 and 2.
Figure 5:
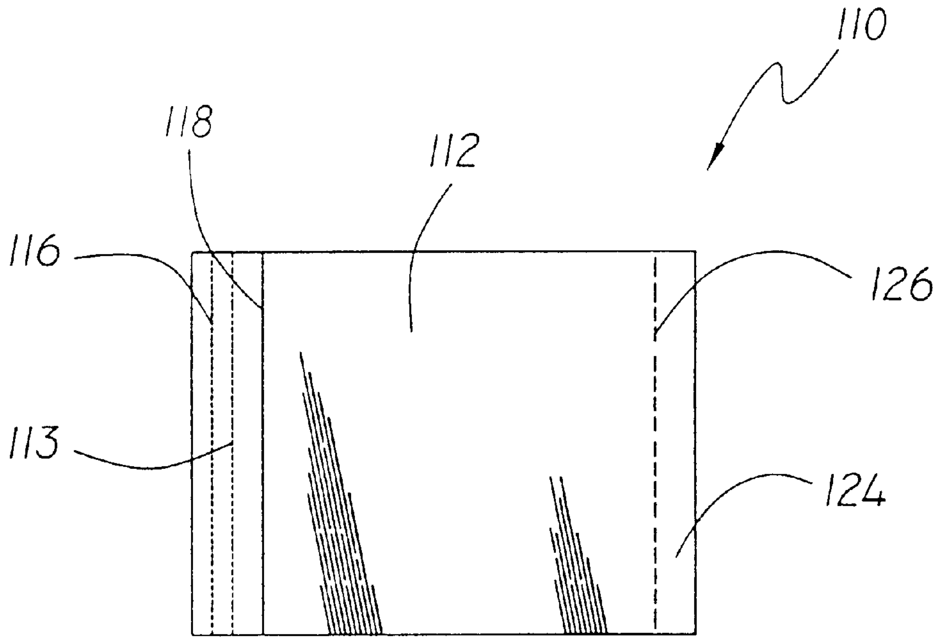
FIG. 5 is a plan view of an alternative dressing according to the present invention.

FIGS. 4 and 5 illustrate an alternative embodiment of the adhesive composite dressings according to the present invention. One variation in the dressing 110 is that the handle 118 is attached to the top face of the backing 112, i.e., on the opposite face on which the pressure sensitive adhesive 114 is located. The handle 118 preferably extends beyond the edge 113 of the backing 112 as best seen in FIG. 4. Another variation is that the dressing 110 does not include a notch designed to adapt the dressing 110 for placement over a catheter or other device.

As with the dressing 10 described in connection with FIGS. 1 and 2, it is preferred that the bond strength between the handle 118 and the backing 112 preferably be stronger than the bond strength between the release surface of the liner 116 and the pressure-sensitive adhesive 114. As a result, a user can grasp the handle 118 and the tab portion 117 of the liner 116 to separate the release surface of the liner 116 from the pressure-sensitive adhesive 114 and backing 112.

The bond strength between the release surface of the liner 116 and the pressure-sensitive adhesive 114 along the edge of the backing 112 is greater than the bond strength between the release surface of the liner 116 and the pressure-sensitive adhesive 114 over the remainder of the backing 112. As a result, a user can deliver the backing 112 and pressure-sensitive adhesive 114 by holding the backing 112 taut between the handle 118 and the liner 116 in a manner similar to that discussed above with respect to dressing 10.

In those dressings in which a line of weakness 126 is provided in the backing 112, it may be preferred that the bond strength between the liner 116 and the pressure-sensitive adhesive 114 along the edge of the backing 112 (generally corresponding to the area of the delivery strip 124) be greater than the tensile strength of the backing 112 across the line of weakness 126. As a result, after application of the backing 112 and pressure-sensitive adhesive 114 to the skin of a patient, the liner 116 can be removed by separating the backing 112 along the line of weakness 126. At the opposite edge of the backing 112, it is also preferred that the handle 118 be removable from the backing 112. The handle 118 may be removed by using a line of weakness or by releasably bonding the handle 118 to the pressure sensitive adhesive 114 as described in connection with dressing 10 above.

A removable handle 118 may alternatively be attached to the backing 112 using a releasable heat seal bond. Such releasable heat seal bonds are described in, e.g., U.S. Pat. No. 5,738,642 (Heinecke et al.). Briefly, however, any releasable heat seal bond should be secure, yet releasable, i.e., the handle 118 and backing 112 can be separated without destroying the integrity of the backing 112 or the bond between the pressure sensitive adhesive 114 on the backing 112 and the skin of a patient. That is, the bond strength between the handle 118 and the backing 112 is lower than the bond strength between the adhesive 114 and the skin of a patient. In addition, the bond between the handle 118 and the backing 112 should be stronger than the bond between the adhesive 114 and the liner 116 to facilitate separation of the liner 116 from the pressure sensitive adhesive 114 during delivery.

Figure 6:
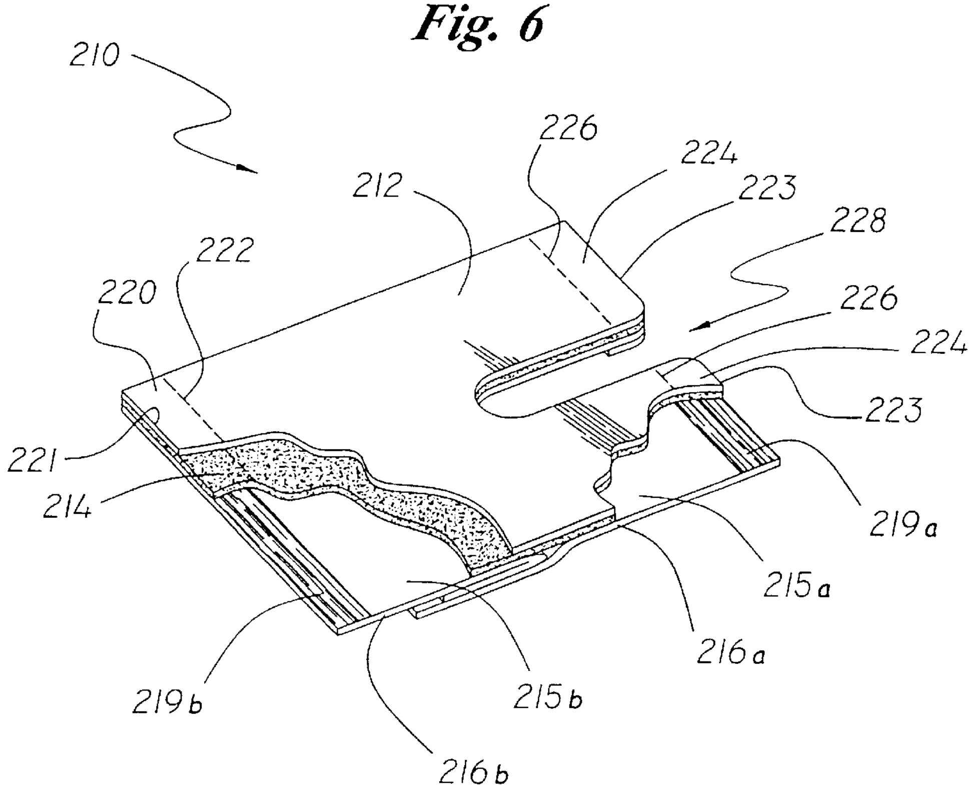
FIG. 6 is a perspective view of one dressing according to the present invention including an abraded two-part liner.

FIG. 6 illustrates another dressing 210 according to present invention that includes a backing 212 and pressure sensitive adhesive 214. Although optional, the illustrated dressing 210 includes a notch 228 opening along the first edge 223 of the backing 212. The notch 228 is preferably adapted to fit over a catheter or other similar medical device.

The pressure sensitive adhesive 214 is protected before delivery by a two-part liner including liner sheets 216*a* and 216*b*. The two liner sheets 216*a* and 216*b* are preferably, but not necessarily provided with a J-fold to assist a user in grasping the liner sheets 216*a* and 216*b* to deliver the dressing 210. It is further preferred that the liner sheet 216*a,* through which the notch 228 is formed, extend towards the opposite edge 221 of the backing 212 far enough to contain the entire notch 228. In other words, the apex of the notch 228 is preferably formed in the liner sheet 216*a.*

The liner sheet 216*a* includes a release surface 215*a* in contact with a portion of the pressure sensitive adhesive 214 on backing 212 and a first retention surface 219*a* in contact with the pressure sensitive adhesive 214 near the edge 223 of the backing 212. The strength of the bond between the pressure sensitive adhesive 214 and the retention surface 219*a* is greater than the strength of the bond between the pressure sensitive adhesive 214 and the release surface 215*a*. The retention surface 219*a* can be formed by, e.g., abrasion, embossing, abrasion and embossing, etc. in which the release coating on the liner sheet 216*a* is disrupted.

The backing 212 may include a line of weakness 226 if the bond between the retention surface 219*a* and pressure sensitive adhesive 214 is not releasable without excessive stretching of the backing 212. The line of weakness 226 and the first edge 223 of the backing 212 define a delivery strip 224 as illustrated in the drawing. It is preferred that the retention surface 219*a* be located substantially within the area of the delivery strip 224, if provided.

The liner sheet 216*b* is constructed similar to the liner sheet 216*a* above and includes a release surface 215*b* and retention surface 219*b* in contact with the pressure sensitive adhesive 214 near the edge 221 of the backing 212. The illustrated backing 212 also includes an optional line of weakness 222 defining a delivery strip 220. The details regarding the construction of that side of the dressing 210 are the same as those described with respect to the side of the dressing including liner 216*a* above.

Because of the differential bonding strengths between the release surfaces 215*a*/215*b* and the retention surfaces 219*a*/219*b*, the backing 212 of the dressing 210 can be delivered in a manner similar to that illustrated in FIG. 2. In other words, the user can grasp both liner sheets 216*a* and 216*b* and pull them in opposite directions until the lines of release between the pressure sensitive adhesive 214 and the liner sheets 216*a* and 216*b* reach the retention surfaces 219*a* and 219*b*. At that point the backing 212 can be held taut between the two liner sheets 216*a* and 216*b*, with the pressure sensitive adhesive 214 adhered to the retention surfaces 219*a* and 219*b*. The dressing can then be placed in a desired location and the backing 212 smoothed down to adhere the exposed pressure sensitive adhesive 214 to the patient's skin.

After location of the backing 212 on a patient, the retention surfaces 219*a* and 219*b* can be separated from the pressure sensitive adhesive 214. In dressings in which the bond between the retention surfaces 219*a* and 219*b* is higher, the backing 212 can be separated along the lines of weakness 222 and 226 by placing further tension on the backing 212 using the liner sheets 216*a* and 216*b*. In those dressings, the tensile strength of the backing 212 across the lines of weakness 222 and 226 is preferably less than the strength of the bond between the pressure sensitive adhesive 214 and the respective retention surface 219*a* or 219*b*. As a result, increasing the tension in the backing 212 using the liner sheets 216*a* and 216*b* typically causes separation of the backing 212 along the corresponding lines of weakness 222 and 226. That separation further results in removal of the corresponding delivery strips (220 and/or 224) from the remainder of the backing 212.

Figure 7:
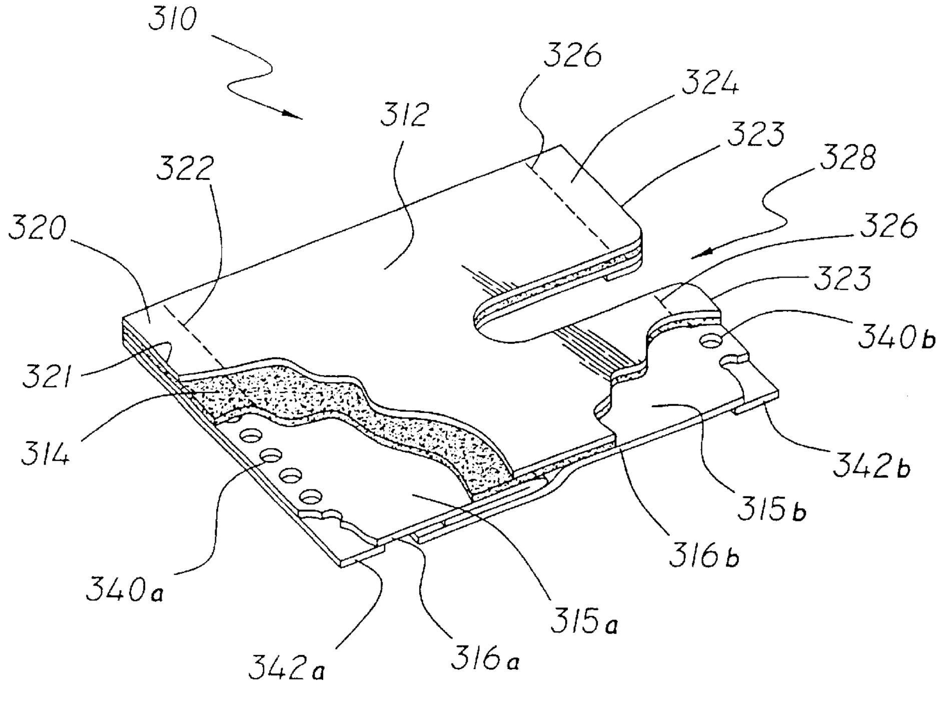
FIG. 7 is a perspective view of another dressing according to the present invention including a two-part liner with voids formed therein.

FIG. 7 illustrates another dressing 310 according to present invention that includes a backing 312 and pressure sensitive adhesive 314. Although optional, the illustrated dressing 310 includes a notch 328 opening along the first edge 323 of the backing 312. The notch 328 is preferably adapted to fit over a catheter or other similar medical device.

The pressure sensitive adhesive 314 is protected before delivery by a two-part liner including liner sheets 316*a* and 316*b*. The two liner sheets 316*a* and 316*b* are preferably, but not necessarily provided with a J-fold to assist a user in grasping the liner sheets 316*a* and 316*b* to deliver the dressing 310. It is further preferred that the liner sheet 316*a*, through which the notch 328 is formed, extend towards the opposite edge 321 of the backing 312 far enough to contain the entire notch 328. In other words, the apex of the notch 328 is preferably formed in the liner sheet 316*a*.

The liner sheet 316*a* includes a release surface 315*a* in contact with a portion of the pressure sensitive adhesive 314 on backing 312 and at least one void 340*a* formed completely through the liner sheet 316*a*. As illustrated in FIG. 7, it is preferred that a plurality of voids 340*a* be formed along the edge of the liner sheet 316*a* proximate the edge 321 of the backing 312. It is further preferred that, where a line of weakness 322 is provided in the backing 312, all of the voids 340*a* be located within the delivery strip 320 defined by the line of weakness 322 and the edge 321 of the backing 312.

A retainer 342*a* can be located over the voids 340*a* in the liner sheet 316*a* such that the portions of the pressure sensitive adhesive 314 exposed by the voids 340*a* bond with the portions of the retainer 342*a* located over the voids 340*a*. The strength of the bond between the pressure sensitive adhesive 314 and the retainer 340*a* is greater than the strength of the bond between the pressure sensitive adhesive 314 and the release surface 315*a* on the liner sheet 316*a*. It is preferred, but not required, that the retainer 342*a* also be bonded to the liner sheet 316*a* (on the opposite face from the release surface 315*a*). It may be further preferred that the retainer 342*a* itself include a pressure sensitive adhesive on the surface facing the liner sheet 316*a* to bond the retainer 342*a* to the liner sheet 316*a*. That additional adhesive on the retainer 342*a* may also enhance the bond between the retainer 342*a* and the pressure sensitive adhesive 314 on the backing.

The opposing edge 323 of the backing 312 includes a similar construction including voids 340*b* formed in the other liner sheet 316*b* and a retainer 342*b* bonded to the pressure sensitive adhesive 314 exposed within the voids 340*b*. Although not explicitly illustrated in FIG. 7, it will be understood that voids 340*b* are formed on each side of the notch 328 along the edge 323 of the dressing 310. It is further preferred that, where a line of weakness 326 is located proximate the edge 323, the voids 340*b* be located within the delivery strip 324 defined by the line of weakness 326 and the edge 323 of the backing 312.

As along edge 321 of the backing 312, the strength of the bond between the pressure sensitive adhesive 314 and the retainer 340*b* is greater than the strength of the bond between the pressure sensitive adhesive 314 and the release surface 315*b* on the liner sheet 316*b*. It is preferred, but not required, that the retainer 342*b* also be bonded to the liner sheet 316*b* (on the opposite face from the release surface 315*b*).

It may be further preferred that the retainer 342*b* itself include a pressure sensitive adhesive on the surface facing the liner sheet 316*b* to bond the retainer 342*b* to the liner sheet 316*b*. That additional adhesive on the retainer 342*b* may also enhance the bond between the retainer 342*b* and the pressure sensitive adhesive 314 on the backing 312.

Because of the differential bonding strengths between the release surfaces 315*a*/315*b* and the retainers 342*a*/342*b*, the backing 312 of the dressing 310 can be delivered in a manner similar to that illustrated in FIG. 2. In other words, the user can grasp both liner sheets 316*a* and 316*b* and pull them in opposite directions until the lines of release between the pressure sensitive adhesive 314 and the liner sheets 316*a* and 316*b* reach the voids 340*a* and 340*b*. At that point the backing 312 can be held taut between the two liner sheets 316*a* and 316*b*, with the pressure sensitive adhesive 314 adhered to the retainers 342*a* and 342*b* through the voids 340*a* and 340*b* in the liners sheets 316*a* and 316*b*. The dressing can then be placed in a desired location and the backing 312 located between the lines of weakness 322 and 326 smoothed down to adhere the exposed pressure sensitive adhesive 314.

After location of the backing 312 on a patient, the liner sheets 316*a* and 316*b* and the retainers 342*a* and 342*b* can be separated from the pressure sensitive adhesive 314. In dressings in which the bond between the retainers 342*a* and 342*b* is higher, the backing 312 is preferably separated along the lines of weakness 322 and 326 by placing further tension on the backing 312 using the liner sheets 316*a* and 316*b*. In this embodiment, the tensile strength of the backing 312 across the lines of weakness 322 and 326 is preferably less than the strength of the bond between the pressure sensitive adhesive 314 and the respective retainers 342*a* or 342*b* through the respective voids 340*a* or 340*b*. As a result, increasing the tension in the backing 312 using the liner sheets 316*a* and 316*b* typically causes separation of the backing 312 along the corresponding lines of weakness 322 and 326.

In a further variation, the dressing 310 could be provided without the retainers 342*a* and 342*b* placed over the voids 340*a* and 340*b*. Increased bond strength is obtained in those dressings at the areas around the voids 340*a* and 340*b* by interaction of the pressure sensitive adhesive 314 with the edges of the voids. As discussed above, the lines of weakness 322 and 326 are optional depending on the strength of the bonds between the liner sheets 316*a* and 316*b* at the edges of the backing 312.

In some respects, the voids 340*a* and 340*b* provided in liner sheets 316*a* and 316*b* (and retainers 342*a* and 342*b*, if present) define retention surfaces as discussed above with respect to the abraded and embossed liners and handles discussed above. Like the retention surfaces discussed above, the retention surfaces defined by the voids 340*a* and 340*b* provide increased bonding to the pressure sensitive adhesive 314 as compared to the strength of the bonds between the release surfaces 315*a* and 315*b*. In one respect, the voids 340*a* and 340*b* can be thought of as disrupting the continuity of the release coating, resulting in a retention surface having a discontinuous release coating that contributes to increased adhesion between the liner sheets and the pressure sensitive adhesive in the area of the voids.

All of the dressings described above include optional notches formed therein to assist in placement of the dressings over a catheter insertion site. All of the notches in the dressings open on an edge of the dressing along which the bond strength between the pressure sensitive adhesive on the backing and the liner or retainer is increased as compared to the strength of the bond between the pressure sensitive adhesive and the remainder of the liner. In some of the embodiments described above, the means for increasing the bond strength between the liner and the pressure sensitive adhesive proximate the edge is an abraded liner surface. In other embodiments, the means for increasing the bond strength takes the form of one or more voids in the liner, through which a retainer is adhered to the pressure sensitive adhesive. The retainer serves to effectively increase the strength of the bond between the liner and pressure sensitive adhesive by interfering with removal of the liner from the pressure sensitive adhesive in the area around the void or voids.

Although two illustrative examples of means for increasing the bond strength between the pressure sensitive adhesive and the liner are provided herein, when used in connection with a notched dressing, the present invention may also rely on other techniques of increasing the bond strength between a pressure sensitive adhesive on a backing and a liner. Examples of other suitable techniques include those described in, e.g., U.S. Pat. Nos. Re. 33,353 (Heinecke); U.S. Pat. No. 4,513,739 (Johns); U.S. Pat. No. 5,153,040 (Faasse, Jr.); and U.S. Pat. No. 5,520,629 (Heinecke et al.).

Any technique that results in increased bond strength between a liner and a backing/pressure sensitive adhesive composite along an edge that includes a notch opening can provide the advantage of assisting in the placement of the dressing over a catheter insertion site. The dressings provide that advantage by allowing the user to maintain tension on both portions of the backing that flank the notch formed therein. By maintaining tension on those backing portions, smooth, aseptic delivery of the dressing is enhanced. The specific techniques of increasing bond strength using abraded liner surfaces, embossed liners, and/or liner voids can, however, provide additional advantages as compared to those techniques of increasing bond strength as discussed in the patents listed above.

For example, the techniques of increasing bond strength as specifically discussed herein (abrasion/embossing/perforating) provide advantages in terms of manufacturing cost and simplicity by allowing the dressings to be manufactured with a single liner material having a release coating over one entire surface, thereby reducing inventory requirements. Furthermore, the operations (abrasion, embossing, perforating, etc.) used to disrupt the continuity of the release coating on the liner can typically be performed in-line with other converting processes, further simplifying manufacturing and reducing cost.

Figure 8:
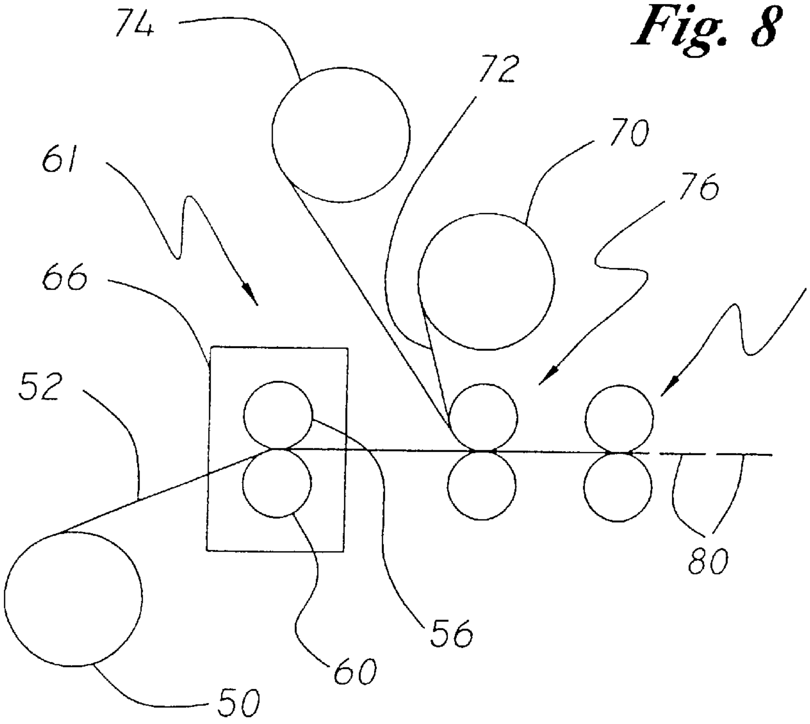
FIG. 8 is a schematic diagram of one process for manufacturing dressings with an abraded liner according to the present invention.

FIG. 8 is a schematic diagram of one method of manufacturing adhesive composite dressings 80 according to the present invention. The method and system depicted in FIG. 8 include a supply of liner 50, including a release surface 52. The liner 50 is preferably directed into a station 61 where a portion of the release surface 52 of the liner 50 is abraded and/or embossed to disrupt the release coating. If the liner 50 is abraded, it is preferred that the station 61 also include an enclosure 66 in which a vacuum is provided to remove debris generated by the abrasion process. After the liner 50 has been abraded and/or embossed, it is directed into a nip roll station 76 along with a supply of backing 70 including a pressure-sensitive adhesive 72 on one surface thereof and a handle material supply 74. The resulting composite, which includes a release liner, pressure-sensitive adhesive, handle, and backing, is then directed into a sheeting station 78 where individual adhesive composite dressings 80 are sheeted from the web. The sheeting station 78 may also be used to form notches in the dressings 80 if so desired. Alternatively, the notches may be formed after lamination of the liner 50 and backing 70 and before sheeting if so desired.

Figure 9:
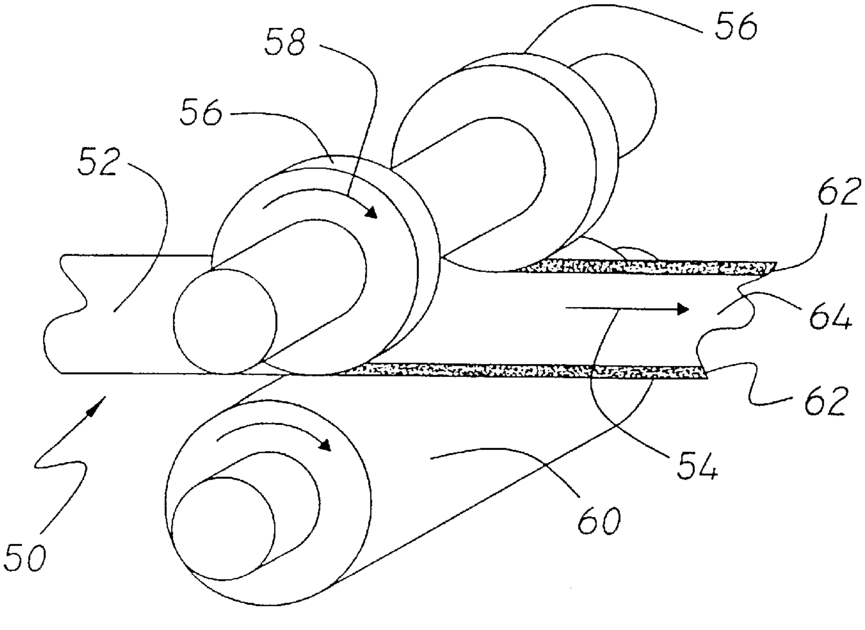
FIG. 9 is an illustration of one abrading process for abrading a liner.

FIG. 9 is a diagram of one particular abrasion process useful in producing adhesive composite dressings according to the present invention. The depicted process involves directing a release liner 50 having a release surface 52 into a nip formed by a pair of abrasion rolls 56 rotating in direction 48. The abrasion rolls 56 are preferably forced against a backing roll 60 that is rotating in the direction 54 in which the liner 50 is moving. The composition of the abrasion rolls 56 can vary, although it is preferred that they have a sufficiently rough surface to remove the release coating 52 on the liner 50. Examples of suitable abrasion rolls 56 can be manufactured from abrasive materials such as those marketed under the tradename SCOTCHBRITE™ Paint & Varnish Remover (Catalog No. 9414NA) by Minnesota Mining and Manufacturing Company, St. Paul, Minn.

As a result of the operation of the abrasion rolls 56 on the liner 50, a central area 64 of the liner 50 remains coated with the release coating while the release coating in areas 62 on each edge of the release liner 50 is at least partially removed. After abrading, the liner 50 can be slit along the machine direction to supply either a handle and liner sheet combination as depicted in, for example, FIG. 1 or the liner 50 can be slit along the machine direction and folded to form a two-part liner as illustrated in, for example, FIG. 6.

If embossing is used in place of abrasion, the edges of the liner 50 can be embossed in a manner similar to that depicted in the abrasion process illustrated in FIG. 9. As discussed above, the embossing disrupts continuity of the release coating on the liner to increase adhesion to the pressure sensitive adhesive on the backing film. It may be advantageous to beat one or both rolls used in embossing to assist in disrupting the release coating.

Figure 10:
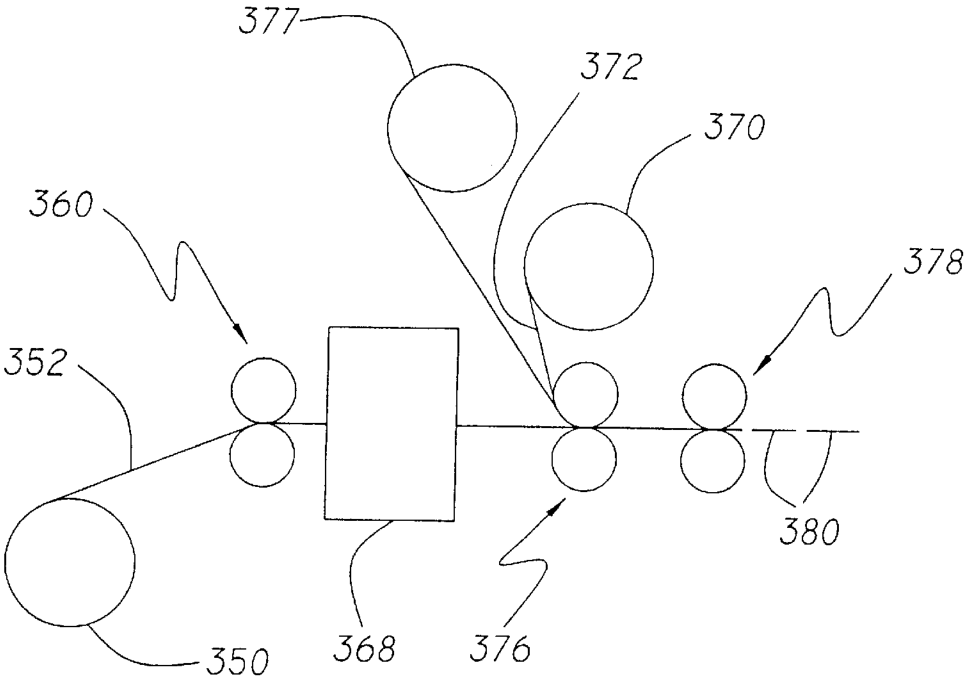
FIG. 10 is a schematic diagram of one process for manufacturing dressing with a perforated liner according to the present invention.

FIG. 10 is a schematic diagram of another method of manufacturing adhesive composite dressings 380 according to the present invention. The method and system depicted in FIG. 10 include a supply of liner 350 including a release surface 352. The liner 350 is preferably directed into a station 360 where a series of voids can be formed in the liner 350. After the liner 350 has been perforated, it is directed into a slitting station 368 where the liner 350 can be slit along the machine direction and a J-fold formed in one side of the slit liner 350. After slitting and folding, the liner 350 is directed into a nip roll station 376 along with a supply of backing 370 including a pressure-sensitive adhesive 372 on one surface thereof and a supply of retainer material 377. The resulting composite, which includes a backing, pressure sensitive adhesive, release liner, and retainers, is then directed into a sheeting station 378 where individual adhesive composite dressings 380 are sheeted from the web.

Figure 11:
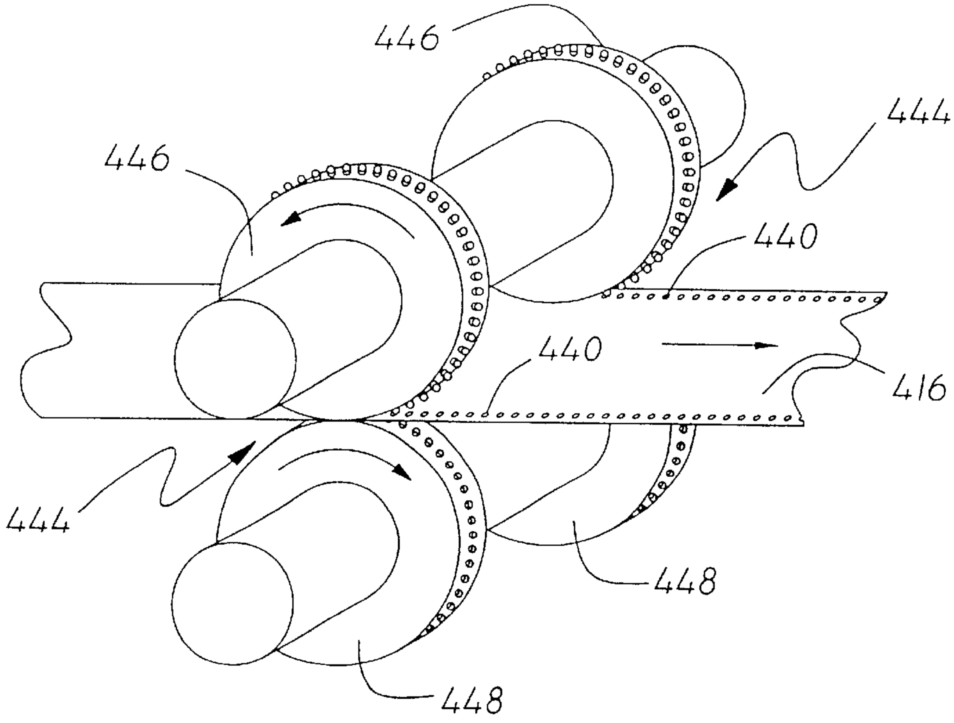
FIG. 11 is a schematic diagram of one process for perforating a liner.

FIG. 11 illustrates one process of forming voids 440 in a continuous web of liner 416 using two perforating nip stations 444. Each of the perforating nip stations 444 includes a male and female die roll 446 and 448, respectively, that mesh to form the desired voids in the liner 416. Other methods of forming voids in sheet material will be known to those skilled and the art and may be substituted for the illustrated apparatus and method.

Although various illustrative embodiments of dressings and methods of manufacturing the same have been described above, it should be understood that additional variations are possible. As one example, additional components may be added to the dressings, such as the catheter support strips discussed in U.S. Pat. No. 5,520,629. Furthermore, although the dressings illustrated above are generally rectangular in shape, dressings according to the present invention may be manufactured with any desired shape.

The patents, patent documents, and publications cited herein are incorporated by reference in their entirety, as if each were individually incorporated by reference. Various modifications and alterations of this invention, other than those explicitly discussed above, will become apparent to those skilled in the art without departing from the scope of this invention, and it should be understood that this invention is not to be unduly limited to the illustrative embodiments set forth herein.

What is claimed is:

1. An adhesive composite dressing comprising:

a backing having top and bottom faces and opposing first and second edges;

a pressure sensitive adhesive located on the bottom face of the backing;

a liner comprising a release surface and a retention surface, the retention surface including a discontinuous release coating that is embossed, wherein the retention surface is attached to the pressure sensitive adhesive along the first edge of the backing; and a handle attached to the backing along the second edge of the backing.

2. A dressing according to claim 1, further comprising a notch formed in the backing, pressure sensitive adhesive, and liner, wherein the notch opens along the first edge of the backing and extends towards the second edge of the backing.

3. An adhesive composite dressing comprising:

a backing having top and bottom faces and opposing first and second edges;

a pressure sensitive adhesive located on the bottom face of the backing;

a first liner sheet including a first release surface attached to a portion of the pressure sensitive adhesive and a first retention surface including a discontinuous release coating that is embossed, the first retention surface being attached to the pressure sensitive adhesive along the first edge of the backing, wherein the strength of the bond between the first retention surface and the pressure sensitive adhesive is greater than the strength of the bond between the first release surface and the pressure sensitive adhesive; and a second liner sheet including a second release surface attached to a portion of the pressure sensitive adhesive and a second retention surface including a discontinuous release coating that is embossed, the second retention surface being attached to the pressure sensitive adhesive along the second edge of the backing, wherein the strength of the bond between the second retention surface and the pressure sensitive adhesive is greater than the strength of the bond between the second release surface and the pressure sensitive adhesive.

4. An adhesive composite dressing comprising:

a backing having top and bottom faces and opposing first and second edges;

a pressure sensitive adhesive located on the bottom face of the backing;

a liner including a release surface attached to the pressure sensitive adhesive and a void formed through the liner, the void exposing a portion of the pressure sensitive adhesive, wherein the bond strength between the liner and the pressure sensitive adhesive is increased proximate the void.

5. A dressing according to claim 4, further comprising a retainer attached to the exposed portion of the pressure sensitive adhesive through the void in the liner, wherein the strength of the bond between the retainer and the pressure sensitive adhesive is greater than the strength of the bond between the release surface and the pressure sensitive adhesive.

6. A dressing according to claim 5, wherein the retainer is attached to the liner.

7. An adhesive composite dressing comprising:

a backing having top and bottom faces and opposing first and second edges;

a pressure sensitive adhesive located on the bottom face of the backing;

a first liner sheet including a first release surface attached to a portion of the pressure sensitive adhesive and a first void exposing a first portion of the pressure sensitive adhesive; and a second liner sheet including a second release surface attached to a portion of the pressure sensitive adhesive and a second void exposing a portion of the pressure sensitive adhesive.

8. A dressing according to claim 7, further comprising:

a first retainer attached to the portion of the pressure sensitive adhesive exposed through the first void in the first liner sheet, wherein the strength of the bond between the first retainer and the pressure sensitive adhesive is greater than the strength of the bond between the first release surface and the pressure sensitive adhesive; and a second retainer attached to the portion of the pressure sensitive adhesive exposed through the second void in the second liner sheet, wherein the strength of the bond between the second retainer and the pressure sensitive adhesive is greater than the strength of the bond between the second release surface and the pressure sensitive adhesive.

9. A dressing according to claim 8, wherein the first retainer is attached to the first liner sheet and the second retainer is attached to the second liner sheet.

10. A dressing according to claim 1, wherein the handle is removably attached to the top face of the backing.

11. A dressing according to claim 1, further comprising a first line of weakness in the backing proximate the first edge of the backing.

12. A dressing according claim 11, wherein the tensile strength of the backing across the first line of weakness is less than the strength of the bond between the pressure sensitive adhesive and the retention surface on the liner.

13. A dressing according to claim 1, wherein the handle includes an abraded surface, and further wherein the abraded surface of the handle is attached to the pressure sensitive adhesive along the second edge of the backing.

14. A dressing according to claim 1, further comprising a second line of weakness in the backing proximate the second edge of the backing.

15. A dressing according to claim 3, further comprising a first line of weakness in the backing proximate the first edge of the backing and a second line of weakness proximate the second edge of the backing.

16. A dressing according claim 15, wherein the tensile strength of the backing across the first line of weakness is less than the strength of the bond between the pressure sensitive adhesive and the first retention surface on the first liner sheet; and wherein the tensile strength of the backing across the second line of weakness is less than the strength of the bond between the pressure sensitive adhesive and the second retention surface on the second liner sheet.

17. An adhesive composite dressing comprising:

a backing having top and bottom faces and opposing first and second edges;

a pressure sensitive adhesive located on the bottom face of the backing;

a liner comprising a release surface and a retention surface, the retention surface including a discontinuous release coating that is abraded, wherein the retention surface is attached to the pressure sensitive adhesive along the first edge of the backing; and a handle attached to the backing along the second edge of the backing.

18. A dressing according to claim 17, further comprising a notch formed in the backing, pressure sensitive adhesive, and liner, wherein the notch opens along the first edge of the backing and extends towards the second edge of the backing.

19. A dressing according to claim 17, wherein the handle is removably attached to the top face of the backing.

20. A dressing according to claim 17, further comprising a first line of weakness in the backing proximate the first edge of the backing.

21. A dressing according to claim 20, wherein the tensile strength of the backing across the first line of weakness is less than the strength of the bond between the pressure sensitive adhesive and the retention surface on the liner.

22. A dressing according to claim 17, wherein the handle includes an abraded surface, and further wherein the abraded surface of the handle is attached to the pressure sensitive adhesive along the second edge of the backing.

23. A dressing according to claim 17, further comprising a second line of weakness in the backing proximate the second edge of the backing.

24. An adhesive composite dressing comprising:

a backing having top and bottom faces and opposing first and second edges;

a pressure sensitive adhesive located on the bottom face of the backing;

a first liner sheet including a first release surface attached to a portion of the pressure sensitive adhesive and a first retention surface including a discontinuous release coating that is abraded, the first retention surface being attached to the pressure sensitive adhesive along the first edge of the backing, wherein the strength of the bond between the first retention surface and the pressure sensitive adhesive is greater than the strength of the bond between the first release surface and the pressure sensitive adhesive; and a second liner sheet including a second release surface attached to a portion of the pressure sensitive adhesive and a second retention surface including a discontinuous release coating that is abraded, the second retention surface being attached to the pressure sensitive adhesive along the second edge of the backing, wherein the strength of the bond between the second retention surface and the pressure sensitive adhesive is greater than the strength of the bond between the second release surface and the pressure sensitive adhesive.

25. A dressing according to claim 24, further comprising a first line of weakness in the backing proximate the first edge of the backing and a second line of weakness proximate the second edge of the backing.

26. A dressing according to claim 25, wherein the tensile strength of the backing across the first line of weakness is less than the strength of the bond between the pressure sensitive adhesive and the first retention surface on the first liner sheet; and wherein the tensile strength of the backing across the second line of weakness is less than the strength of the bond between the pressure sensitive adhesive and the second retention surface on the second liner sheet.

* * * * *

UNITED STATES PATENT AND TRADEMARK OFFICE

CERTIFICATE OF CORRECTION

PATENT NO. : 6,607,799 B1 
DATED : August 19, 2003
INVENTOR(S) : Steven B. Heinecke et al.

It is certified that error appears in the above-identified patent and that said Letters Patent is hereby corrected as shown below:

Column 5,
Line 55, delete “ore” and insert in place thereof -- more --.

Column 8,
Line 59, delete “tie” and insert in place thereof -- the --.

Column 12,
Line 43, “It may be...backing 312.” should be a part of the preceding paragraph.

Column 15,
Line 7, delete “beat” and insert in place thereof -- heat --.

Signed and Sealed this

Twentieth Day of September, 2005

JON W. DUDAS
*Director of the United States Patent and Trademark Office*